US012002579B1

(12) United States Patent
Arkoff et al.

(10) Patent No.: US 12,002,579 B1
(45) Date of Patent: Jun. 4, 2024

(54) WEARABLE MEDICAL DEVICE DATA CONNECTIVITY SYSTEM AND METHOD

(71) Applicant: OneSource Solutions International, INC, Sudbury, MA (US)

(72) Inventors: Harold Arkoff, Sudbury, MA (US); Vedran Jukic, Trieste (IT)

(73) Assignee: OneSource Solutions International, INC, Sudbury, MA (US)

( * ) Notice: Subject to any disclaimer, the term of this patent is extended or adjusted under 35 U.S.C. 154(b) by 0 days.

(21) Appl. No.: 18/518,945

(22) Filed: Nov. 24, 2023

(51) Int. Cl.
*G16H 40/67* (2018.01)
*G08B 5/22* (2006.01)
*G08B 21/02* (2006.01)
*G16H 10/60* (2018.01)
*G16H 40/20* (2018.01)

(52) U.S. Cl.
CPC .............. *G16H 40/67* (2018.01); *G08B 5/22* (2013.01); *G08B 21/0277* (2013.01); *G16H 10/60* (2018.01); *G16H 40/20* (2018.01); *H04Q 2209/43* (2013.01)

(58) Field of Classification Search
CPC ........ G16H 40/67; G16H 10/60; G16H 40/20; G08B 5/22; G08B 21/0277; H04Q 2209/43

USPC .................................................... 340/286.07
See application file for complete search history.

(56) References Cited

U.S. PATENT DOCUMENTS

| | | | | |
|---|---|---|---|---|
| 11,107,590 | B2 * | 8/2021 | Shiibashi | G16H 10/60 |
| 2015/0173614 | A1 * | 6/2015 | Takano | G16H 40/67 600/301 |
| 2015/0173615 | A1 * | 6/2015 | Nagasaki | H04L 67/125 600/301 |
| 2015/0242821 | A1 * | 8/2015 | Arkoff | G06Q 10/1097 705/2 |
| 2018/0302189 | A1 * | 10/2018 | Harrod, IV | H04L 43/16 |
| 2022/0061708 | A1 * | 3/2022 | Southerland, III | A61B 5/7275 |
| 2024/0096460 | A1 * | 3/2024 | Arkoff | G16H 50/20 |

* cited by examiner

*Primary Examiner* — Omar Casillashernandez
(74) *Attorney, Agent, or Firm* — IP Consulting Group; Michael Razavi; Alfred Hoyte, Jr.

(57) ABSTRACT

The inventive system enables wearables to function as portable, always transmitting medical devices within hospital settings, integrating the data therefrom seamlessly into electronic medical records. The dynamic switching of wearables among virtual Bluetooth hotspots ensures and enhances both the reliability of data transmission and the potential for wearables to contribute meaningfully to the electronic medical record infrastructure within healthcare facilities.

11 Claims, 11 Drawing Sheets

WEARABLE MEDICAL DEVICE DATA CONNECTIVITY SYSTEM AND METHOD

FIELD OF THE INVENTION

This application relates to healthcare data management hardware and software, and more particularly to a reliable method and apparatus for connecting medical wearables associated with a mobile patient to data monitoring and storage hardware within a facility.

BACKGROUND

Modern hospitals are complex, technologically sophisticated organizations having sometimes thousands of employees, doctors, nurses, medical technicians, and administrators, with critical life or death decisions being made regularly and sometimes having to be made abruptly and quickly. Up-to-date, perspicuous, and complete data about the patient can make a difference. And even when critical decisions are not at stake, increases in the cost of health care have made it imperative to optimize use of hospital resources and facility personnel. More importantly, the need to minimize adverse events and medical errors by providing hospital personnel with remote access to real-time patient data.

Patient wearables, that is, medical devices that monitor various aspects of a patient's health such as heart rate, rhythm, temperature, blood pressure and glucose monitoring are increasingly being used outside of the hospital for personal use, but not routinely being used in hospitals and other patient care facilities for lack of infrastructure to integrate into hospital information systems and workflow. Wearables are typically designed to only communicate to an individual's personal smartphone via Bluetooth. Wearables have not been designed to communicate with the data infrastructure in hospitals, prohibiting their widespread adoption for use in hospitalized patients. Efficiently collecting data from wearables allows the data therefrom to be more easily integrated into a Medical Data Governance system as described herein.

Accordingly, it would be beneficial to provide a method and apparatus to allow a patient with wearables to roam within or outside a facility, while continuing to transmit data from the wearable to the appropriate storage/processing facility.

SUMMARY

In accordance with the present disclosure, embodiments of a system, method, and apparatus are described which eliminate or ameliorate the problems and disadvantages associated with previous systems, methods, and apparatuses.

Due to the exponential data availability from growing health-related devices, the risk of data not being collected, or worse, being wrongly associated, grows exponentially. In a particular embodiment, the present invention opposes this trend by allowing a patient with a wearable to roam within a facility and continually transmit data in a secure and seamless fashion.

The instant invention provides a simple, stress-free connection and data transmitting scheme for patient wearables requiring no special effort on the patient or hospital staff.

The instant invention provides a method to optimize patient monitoring by utilizing every computing device within a facility or predetermined area as Bluetooth hotspots actively seeking known medical devices. These computing devices act as virtual intelligent routers, continuously searching for and switching wearable devices among them to achieve the best Bluetooth signal strength and ensure the seamless continuity of data from the patient. The inventive system enables wearables to function as portable, always transmitting medical devices within hospital settings, integrating the data therefrom seamlessly into electronic medical records. The dynamic switching of wearables among virtual Bluetooth hotspots ensures and enhances both the reliability of data transmission and the potential for wearables to contribute meaningfully to the electronic medical record infrastructure within healthcare facilities.

The instant invention provides a simple, stress-free connection and data transmitting scheme for patient wearables associated with a patient requiring no special effort on the patient or hospital staff which uses a mobile phone that is not associated with a patient to provide connectivity to facilitate roaming within or outside a facility.

The instant invention provides a simple, stress-free connection and data transmitting scheme for patients which uses a mobile phone to facilitate roaming within or outside a facility, by using the fingerprint of a Bluetooth descriptor connected to the IoMT hub with a mobile phone.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

The present invention concerns a method and apparatus for obtaining data from patient wearables, and ultimately exporting the data to an EMR using the MDGS as herein described. More specifically, the invention allows for patient mobility within or outside any healthcare facility that has an existing medical data governance (MDG) system in place. Our invention is a Bluetooth virtual proxy network comprised of multiple Bluetooth computing devices. When using multiple proxy computing devices together we have created a virtual distributed network of Bluetooth proxy computing devices that become virtual intelligent routers. The real-world application is that a patient can roam within or outside a facility and relay the data from their wearable back to bedside MDDS units via any computing devices in the facility with Bluetooth receiver running the inventive proxy software service. The proxy computing devices can be the patient's personal smartphone, a nearby smartphone from an employee or any computer in the facility that is running this proxy software service. These all work together collectively as a MESH network. In accordance with the method of the instant invention, instead of using bluetooth API of the hardware (the industry standard and custom) by which wearable device data is acquired, stored, analyzed, displayed, and sent to the storage system, these functionalities are virtualized on the host and not the hardware (the phone or the computer). Algorithm processing is not performed on the hardware. The hardware is used only as a relay to acquire the data and the processing occurs on the MDDS units. There is only one footprint for all wearables. Instead of one application for each wearable a patient uses, there is only one application for all wearables. In the inventive scheme, the wearables need not be paired with the patient's phone, although this is an option as will be discussed below.

Figure 1:
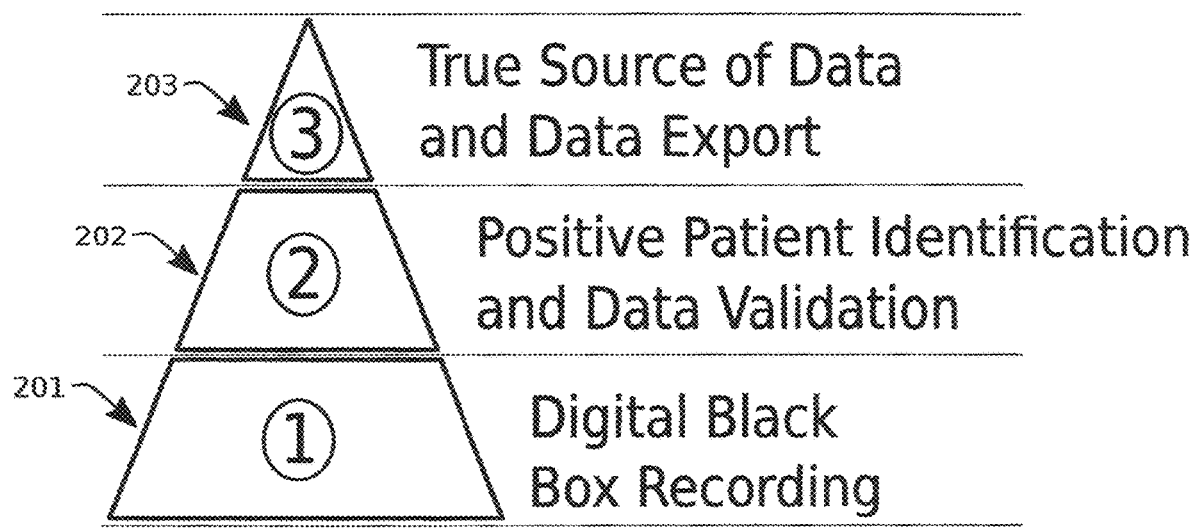
FIG. 1 is a block diagram overview of a Medical Data Governance System.

FIG. 1 is a block diagram overview of the three functional layers of a Medical Data Governance System (MDGS) in an embodiment. The base layer 201 is a digital black box recording of patient data. The middle layer 202 is positive patient identification and data validation. The top layer 203 is true source data and data export for research and other purposes.

Binding Location (geo-localization, indoor localization), Time, Provider, Patient is associated with data obtained from isolated or networked medical and medical relevant devices. The MDGS collects the data from medical devices such as wearables, identifies them, normalizes and time synchronizes all the data outputs while storing them safely, with tamper detection methods (such as blockchain) local to the source of data. Partial and/or metadata about the collected data are used to identify the related patient, patient location, patient provider, source of data and location from whom the data had been collected when available. In the process described as MDGS, the normalized data along with time, time span, location, patient are securely stored and saved for data export into third party systems (data consumers) or stored for later export. The process of binding Location, Time, Provider, Patient to the data can occur pre or post data collection, generating new datasets at each intervention or association, creating incremental dataset groups. For example, complete patient association can be done hours or days after the data has been collected, as well as preset before the data is collected from the medical device.

Patient Treatment Time Optimization and Device Asset Management

MDG provides a true source of data that can highlight the schedule time variations of exams and other medical treatments and provides tools for the rescheduling feedback, contacting and receiving feedback from patients/physician/healthcare professionals thus introducing general system flexibility through the use of lean process and six sigma methods. MDG leverages modern communication methods (phone apps, emails, web services . . . ) and easily links patient and physician/other healthcare professionals to the scheduled use of medical devices. After unexpected events that may cause a miss in scheduled operations, the MDG may create a backup schedule to preemptively fill the gaps and may facilitate healthcare and schedule professionals to optimize machine time usage. This could create a new marketplace for priority services for those patients that opt for it.

Patient/User Data Monetization by Patient/User, Institution, or Combination of

MDG enables patients/users and or Institutions to monetize their vitals, medically relevant data, and other patient data collected during the stay inside the healthcare institution, as well through the extended data collected over a period of time in multiple stays or spot measurements in healthcare institutions. Patients and or Hospitals could establish a relationship with a third party (such as a drug manufacturer, independent drug trials projects, undisclosed trials to the institution) and provide to the third party normalized data collected, organized, and provided by the MDG used by the healthcare institution, and provided to the patient in different standardized formats, even in near real time. The institution might not be aware of the final user of the patient data. MDG can create additional revenue to the institution by monetizing such a service per patient and per data processed. MDG can track and trace data usage per patient and assets. MDG through the export of all specific, validated clinical data, medical relevant data, could create a new data-based economy. Third parties (researchers or corporations) could establish a relationship with individuals or hospitals to provide data through a Federated System for the purpose of research, development, and regulatory approval of new medical grade wearables.

Patient Notification and Pre or Post Consent of Data Use for Second Opinions, Medical Treatments, Specific Research, Validation, Education, or Application.

MDG is solving the problem of giving consent and approval, or notification for use of the patient data for second opinion, medical treatments, specific research, validation projects, and educational purposes. Specific patient or user data is previously screened based on always updated, public, generic, anonymous metadata (for example: sex, age, days in hospital, normalized data content and length: heart rate, respiration rate, drugs, etc.).

Research Dataset Optimization

MDG allows for third party statistical analysis (research) on the whole population dataset, without exporting or providing data to the third party, but rather comparing the result to the legally available consent subset group. A statistically relevant result might indicate a minimal group of statistically significant subset of data to search consent and optimize the time for valid and repeatable dataset.

Data Normalization

Data normalization appears to be a key element for application of Artificial Intelligence in Healthcare. MDG, through the acquisition of higher frequency (sub-minute/sub-seconds), high fidelity data, patient identification, provider identification, data validation, time synchronization, localization of different, non-homogeneous clinical, medical relevant, patient relevant data from isolated, standalone medical devices or networked devices, can provide a superior, in terms of quality and quantity, subset of normalized data.

Metadata

MDG collects, stores, normalizes, and time synchronizes all available data points from any patient related source of data. Metadata such as healthcare provider, environment temperature, hours of operation of medical device, time from last service, related errors can provide almost endless sources of data for future use or research.

An Overall Solution to the Lack of Standards and Interoperability

MDG, as a sole purpose of true source of data, and without any specific end user purpose serves as an interoperability and standardization tool, enabling the health industry to leverage stored data through new and old standards based on the need.

Root-Cause Analysis and Continuous Quality Improvement (CQI) Classification

As a most complete data gathering and presentation tool, any adverse case or event can be studied up to the maximum details recorded by the MDG for Root Cause Analysis in cases of Morbidity and Mortality within a healthcare facility. MDG tools help in retrieving patient identification, provider identification, data validation, time synchronization, localization of different, non-homogeneous clinical, medical, medically relevant, patient relevant data after adverse events, providing tools for analyzing risks, therefore introducing quality, process, outcome improvements. This classifies MDG as a quality improvement tool, therefore protected from legal perspective to be used as proof of malpractice or errors. Non-medical user notification and pre or post consent of data use for specific research, validation, education, marketing, or application. The ability of handling critical data can be extended to several personal user data in different fields outside of medical applications, like sports, fitness, and general health.

Figure 2:
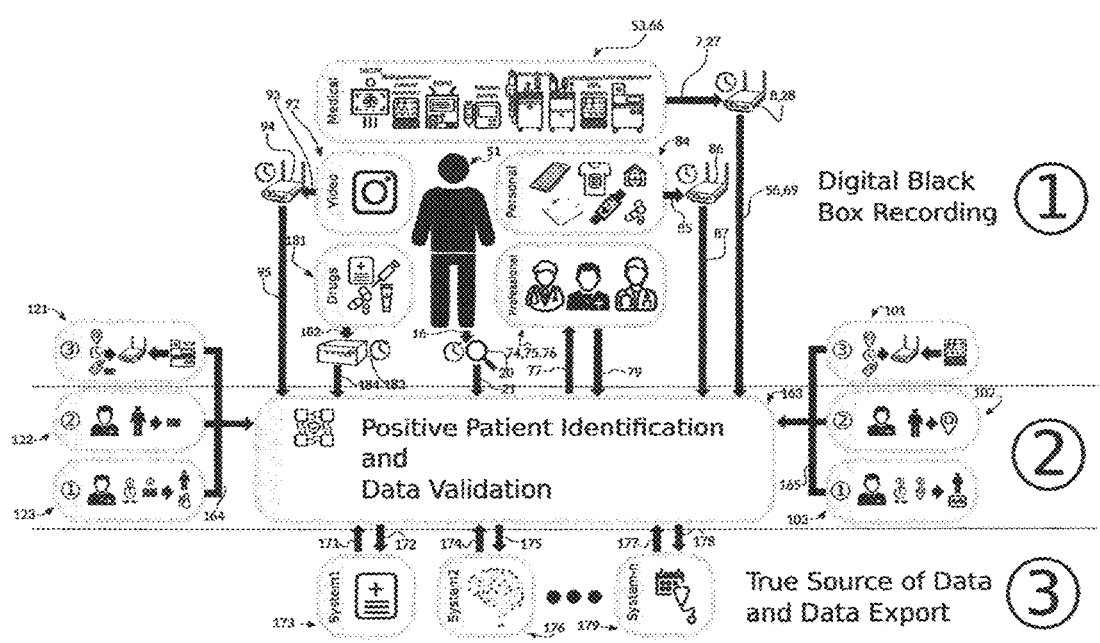
FIG. 2 is an illustration providing high-level detail about each layer of the MDGS pyramid of FIG. 1.

FIG. 2 is an illustration of a simplified 3-layer MDGS in an embodiment. Artificial Intelligence, Machine Learning systems, and Deep Learning Systems all require a medical data governance middleware to assure proper, normalized and verified data inputs. Legacy health information systems and electronic medical records (EMR) were designed to receive only a minute portion of the exponentially increasing data medical devices can create and can be collected. Also, outdated HIS/EMR (Healthcare Information Systems/Electronic Medical Record) and inadequate patient identification and association can cause serious errors in the future of precision medicine, augmented intelligence, and AI, as well as representing a serious bottleneck for data-hungry personalized medicine, real time applications, and in practice, most medical device data are not recorded at all.

Layer (1): Black Box Recording

Data from hospital medical devices, continuous monitoring systems and laboratory devices 53, 66, through the use of proper physical and software drivers 7, 27 are collected by Medical Device Data System (MDDS) devices 8, 28 and location/time synchronized, optionally signed with blockchain service, and made available to the second layer of the MDGS—Positive Patient Identification and Data Validation. Medical Device Data Systems (MDDS) are hardware or software products intended to transfer, store, convert the format of, or display medical device data. A MDDS does not otherwise modify the data or its display, and it does not by itself control the functions or parameters of any other medical device.

Similar to laboratory devices, video 92 can be transferred 93, recorded 94, location/time synchronized, and then transferred when convenient 95 to a central repository and patient locked by the second layer. Wearables and home or community care data and sensors 84, generally available through BLE (Blue Tooth Low Energy, BT4.1) wireless protocol 85, can be registered and time synchronized by a portable MDDS device or phone application 86, and available or optionally transferred 87, when possible, to a central repository.

Professional notes, comments, orders, and communications, generally known as Journaling, 74, 76 can be tracked, reported, and stored 77, 79 via third party systems and solutions.

Drug Distribution, Administration and all other third-party software and systems 181, 182, 183 can be tracked, tagged, stored, time synchronized and made available 184 to the third layer.

Each MDDS has a location 101 and metadata configuration panel available for setup 121 so the medical device data can be location or patient tagged for patient data association and data validation.

Layer (2): Positive Patient Identification (PPI) and Data Validation (DV)

As described below in more detail in the description of FIG. 5, PPI and DV depends on previous location and metadata setup of MDDS 121, 101 (FIG. 2) and proper data entry of metadata 122 or location 102, and active healthcare professional confirmation of patient location time presence 103 or the proper patient identification process 123. Upon PPI and DV, different segments of Digital Black Box recordings are patient and time segment tagged 163 and available to the third layer, True Source of Data and Data Export.

Layer (3): True Source of Data and Data Export

By concentrating all available medical relevant data into a single source and providing a subset of data to each receiving sub-system 173, 176, 179 with the correct source and time reference, the Medical Data Governance System becomes the True Source of Data and guarantees the data consistency through the use of block chain signatures.

Due to the exponential data availability from growing health-related devices, the risk of data not being collected, or worse, being wrongly associated, grows exponentially. The MDGS opposes this trend by using the same data to augment the data affinity and isolate and indicate possible association or data integrity errors.

The MDGS, as the True and Complete Source of Data, should be used as the front end for sub-systems. When errors are detected from automated systems or from a later check or evidence, errors are propagated through related data, and when the data, a wrong association or time reference is corrected and signed with block-chain, the whole time segment of the data must be resent to the sub-system rather than those subsystems being corrected independently.

Each medical subsystem 173, 176, 179 is designed to receive specific data with a specific frequency, quantity, and quality. Sometimes the specific data, frequency, quantity, and quality do not overlap between subsystems. From the Complete True Source of Data, the specific export drivers 171, 172, 174, 175, 177, 178 collect, filter, consistency check, transform and deliver appropriate data to each subsystem.

Figure 3:
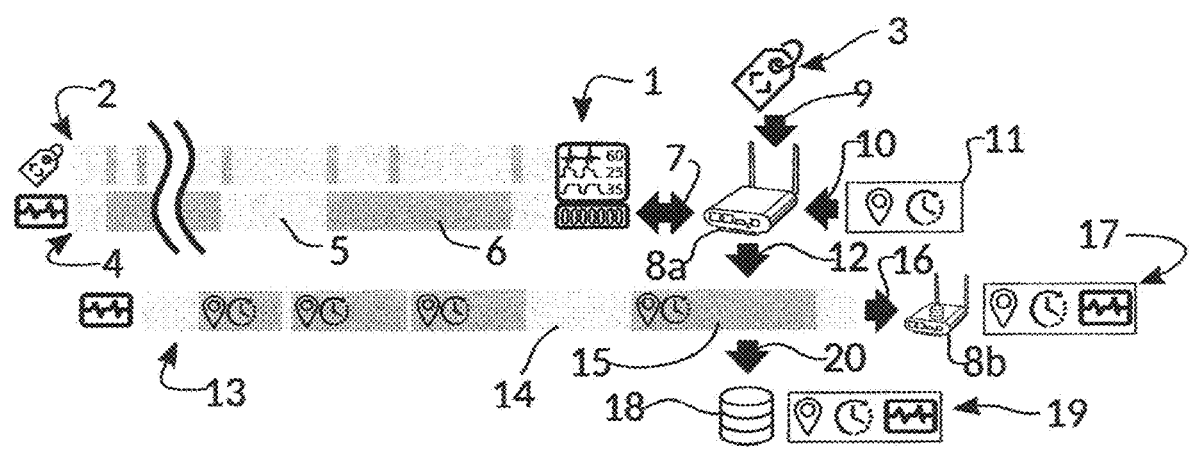
FIG. 3 is an illustration of the details of continuous patient monitoring measurement, part of the first layer of MDGS, Digital Black Box Recording, in an embodiment.

FIG. 3 is a block diagram illustrating details of one component of Layer (1) Digital Black Box Recording, in particular, the medical devices that measure continuous patient data, such as Multiparametric Patient Monitoring, Anesthesia machines, EEG and similar belonging to the "continuous" group of potentially retrievable medical data 4, where the session beginning, duration and therefore, its end can be associated using continuous, complete data flow without data interruption 6. Previous idle, non-patient data that is irrelevant and does not provide any information, except the fact that at that time patient data was not being collected is noted 5. Metadata such as device not ready, cable disconnected, device powered off is recorded 2, including but not limited to room temperature and pressure, video, and other environment data if and when available such as other medical devices connected 3 that provide essential information about the start and stop of the data valid session 6. Medical devices 1 usually have one or more data export mechanisms 7 which are used by a Medical Device Data Systems (MDDS) unit 8a to extract and collect ALL possible data, along with metadata 2, 3 from specific software and hardware drivers and interfaces 9 and along with previously associated 10 location, metadata and clock-time 11 reference.

The MDDS unit 8a, which is a patient bedside unit associated with a particular patient as discussed in more detail below, stores 16 location sessions 15 with all medical data collected, metadata, timestamps and location identifiers 13 and keeps it for a limited time, for example up to 24 hours, before it copies it 20 to a centralized repository 18. Empty, non-relevant data 14 are simply not propagated and ignored.

The MDDS 8b can serve a complete time synchronized and location subset of near real time data 17 without intermediary subsystems, or if the complete dataset had been copied to a centralized repository 18, the past data subset 19 can be retrieved from the repository services 18.

Figure 4:
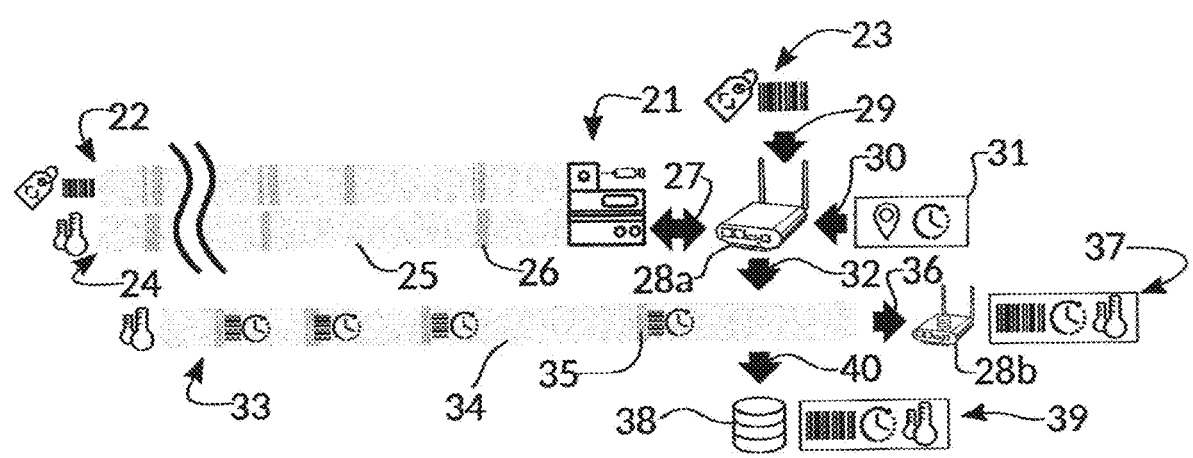
FIG. 4 is an illustration of the details of the recording of sporadic patient related data, part of the first layer of a MDGS, Digital Black Box Recording, in an embodiment.

FIG. 4 is a block diagram illustrating details of another component of Layer (1) Digital Black Box Recording, in particular, medical devices that measure sporadic patient related data 21 such as Blood Gas Laboratory Machines, Generic Laboratory Devices, Portable Non-Invasive Blood Pressure devices, Scales and similar belonging to the "spot" group of potentially retrievable medical data 24. The session beginning, duration and result can be directly associated from meta-data, such as bar code patient ID, Point Of Care (POC) input, and the result 26. Previous idle, non-patient data that is irrelevant and does not provide any information is not propagated, except for the metadata indicating that at that time patient data results were not being collected 25. Metadata is included such as, but not limited to, Patient Bar Code ID, POC input, device not ready, cable disconnected, device powered off 2, but also room temperature and pressure, video, and other environment data such as other medical devices connected 3 that provide essential information about the start and end of the result data 26. Medical devices and Laboratory devices 21 usually have one or more data export mechanisms 27 which are used by a Medical Device Data Systems (MDDS) 28a to extract and collect ALL possible data, along with Metadata 22, 23 from specific software and hardware drivers and interfaces 29 and along with previously associated 30 location, metadata and clock-time reference 31.

The MDDS stores 36 location sessions 35 with all medical data collected, metadata, timestamps, and location identifiers 33 and keeps it for a limited time, for example up to 24 hours, before it copies it 40 to a centralized repository 38. Empty, non-relevant data 34 are simply not propagated and are ignored.

The MDDS can serve a complete time synchronized and location subset of near real time data 37 without intermediary subsystem, or if the complete dataset had been copied to a centralized repository 38, the past data 39 subset can be retrieved from that repository service 38.

In any case, the Layer (1) Digital Black Box Recording does not have Protected Health Information (PHI), and if it is provided, it is stripped off and eliminated from the stored data. The possible PHI is removed from drivers handling specific medical devices.

Blockchain in Signature Anti Tampering Protection

Figure 5:
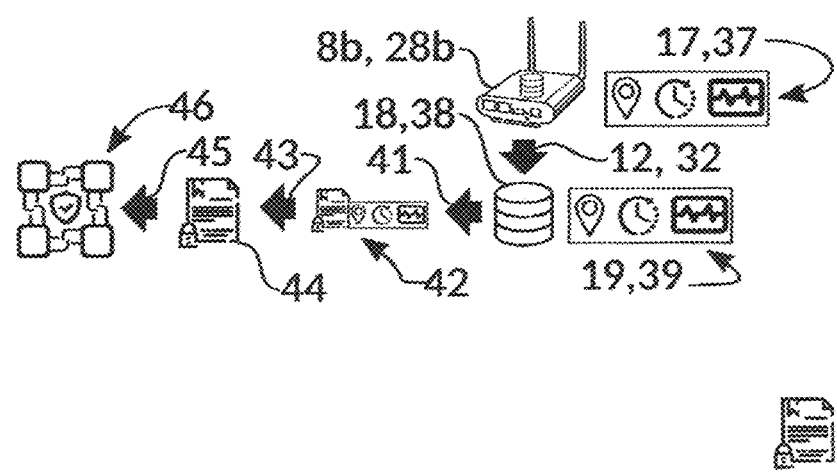
FIG. 5 is an illustration of the details of providing block chain signatures for black box recorded patient data sets in an embodiment.

When the MDDS 8b, 28b transfers the complete time synchronized and location data set 17, 37 to a centralized repository 18, 38, then as depicted in FIG. 5, the past data set 19, 39 is "signed" 41, 42, and the Signature 44 is produced 43. The signature can be transferred 45 or stored to the external Block Chain Server Authority 46 to tamper proof the data collected and have an external safety check for data consistency.

Figure 6:
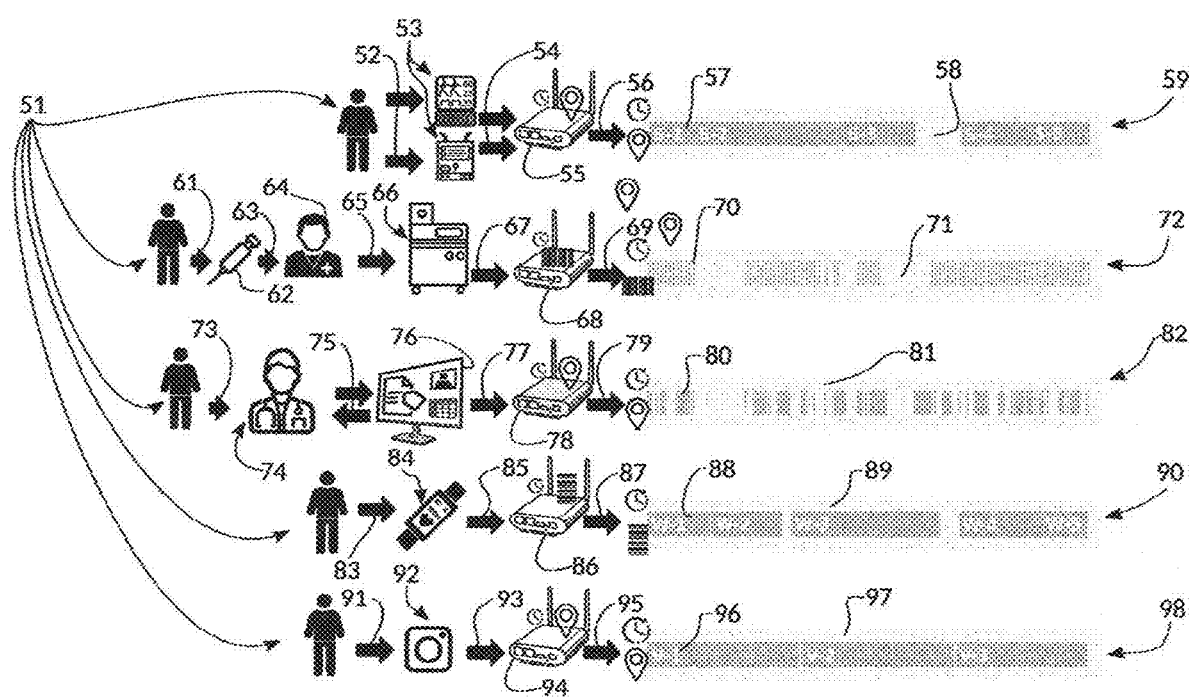
FIG. 6 is an illustration of the details of a black box recording of a variety of different types of patient data in an embodiment.

Electronic Black Box Recording Data Diagrams for Various Medical Data and Medical Relevant Data Sources Different medical and medical relevant data types are recorded, including location and patient ID metadata, and time synchronized with medical device data as depicted in FIG. 6. Continuous medical devices 59, laboratory devices 72, professional journaling and comments 82, personal wearables and fitness trackers 90, and video capture systems 98 store the non PHI (Protected Healthcare Information) only.

Continuous Medical Measurements 59

When patients 51 are connected with physical sensors and or leads 52 to medical devices 53 that have the capability to export real or near real time data 54 to an MDDS 55, the MDDS 55 will timestamp, location and metadata associate the data created 56 with a Digital Black Box Recorder dataset 59 consisting of different data sessions 57 and idle time 58.

Laboratory Data 72

Samples of blood or other patient relevant organic samples 61 are taken and temporary conserved 62 and transported 63 by healthcare professionals 64 then properly processed and electronically identified 65 by laboratory device 66. The lab equipment should have the ability to export metadata such as POC or ID-collected and lab results in an electronic format 67 which is collected and processed by the MDDS 68. The MDDS will timestamp, location, ID and metadata associate the data creating 69 a Digital Black Box Recorder dataset 72 consisting of different laboratory results 70, metadata of patient identification codes and idle time 71. Protected Healthcare Information is stripped off and assure the data to be deidentified matching a single universal identification code to be stored instead if not already provided.

Medical Journaling 82

Every patient 51 consult, visit or opinion 73 between patient 51 and the medical professional 74 can be recorded or have notes taken 75 by third party software or systems 76 and directly exported or queried 77 from the MDDS 78 systems at the place of creation (near the patient current location). The MDDS will timestamp, location, ID and metadata associate the data, creating 79 a Digital Black Box Recorder dataset 82 consisting of various notes and documents, video, and audio notes 80, metadata of patient identification codes and idle time 81. Protected Healthcare Information will be stripped off and ensure the data is deidentified matching a single universal identification code to be stored instead.

Wearables and Fitness Trackers 90

Patient 51 might have 83 various personal wearable devices operating with BLE (blue tooth low energy or similar technologies) 84 that can be periodically or constantly in communication 85 with a fixed or portable MDDS or smartphone MDDS app 86 (see FIG. 6) that has been preprogramed with a constantly updated Bluetooth fingerprint or Blueooth descriptor such as a BLE MAC address, unique identifier code, or serial number to receive and associate the medical devices with the patient. Like the continuous medical measuring 59 and the measure-result laboratory systems 72, data sessions are defined 87 with metadata such as Bluetooth descriptor, patient location, and non-relevant data segments 89. However, with a fixed MDDS such as 8b, 28b, the patient 51 cannot roam within the facility without going out of range of the MDDS. Accordingly, in an embodiment of the invention, a method is provided to allow a patient to roam within a facility while allowing continuous transmission of data from wearables, as will be discussed in more detail below.

Video and Medical Relevant Data 98

Referring now particularly to FIG. 6, all patient 51 relevant video or medically relevant ambient data 92 can be recorded 93, time and location synchronized by the MDDS 94 system. The MDDS 94 will timestamp, location, and metadata associate the video and/or ambient data creating 95 a Digital Black Box Recorder video or ambient dataset 98 consisting of different data session 96 and idle time 97.

Figure 7:
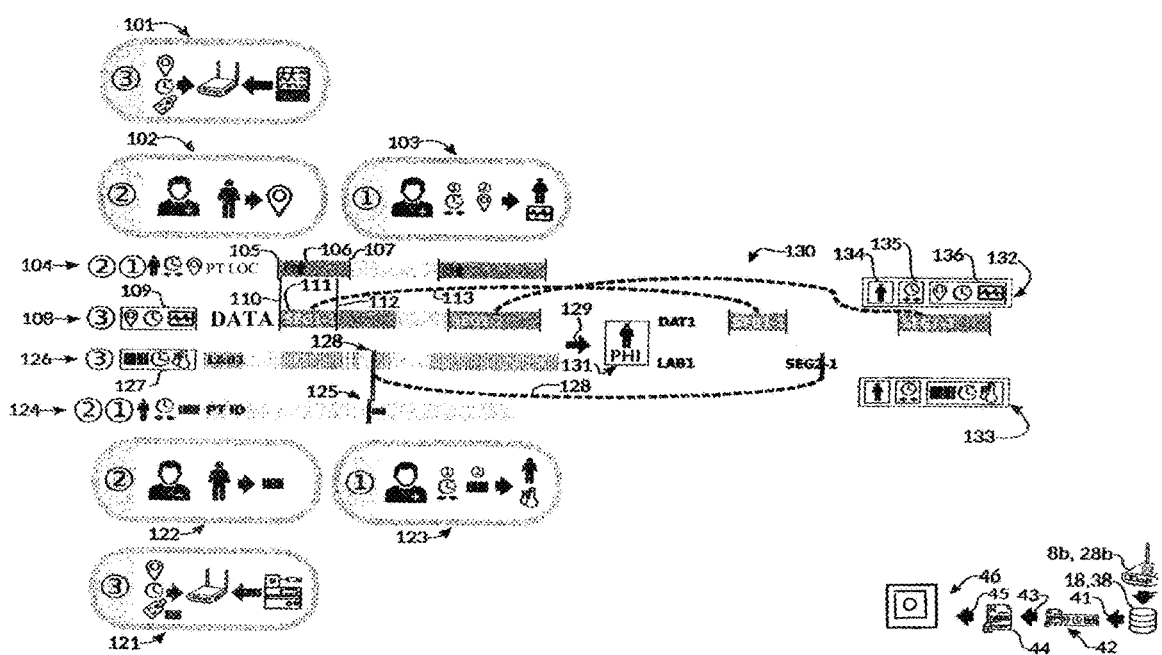
FIG. 7 is an illustration of the details of the second layer of a MDGS, Positive Patient Identification and Data Verification in an embodiment.

Second Layer of Medical Data Governance: Positive Patient Identification and Data Validation FIG. 7 shows the process of association between the patient and the data collected from, e.g., a wearable, or to be collected 101, 121. An external process, software, or system associates a Patient Identification code to a location 102 or patient-to-patient Identification code 122. An active healthcare professional, or someone that has been assigned to verify the patient data, patient location or patient identification, confirms the three key elements of the patient data triplets: patient identification and its code 134, segment, or segments of time the patient was on location 135, and patient data collected at that location 109, 136 throughout the active process 103, 123.

Due to patient location recorded or provided by third party systems 102, 104 and data and metadata collected 101, 108, a subsection defined by start 105 and stop time 107, identified by a healthcare professional 106 or by third-party systems allows the precise selection of the appropriate and consistent data session 111 and seamlessly finetunes the accurate start 110 and stop 112 of the particular data session 113, then creates the building block of triplets 132 that constitutes a complete positive patient identification and data validation record 130.

For a laboratory, or multi patient systems such as laboratory machines, an action that immediately precedes or clearly relates to the result being consecutively transferred and collected by the MDDS system 121, a previously created Patient Identification code 122 is collected as metadata and time synchronized with the result that is collected. An active process of confirming the data 128, patient and patient id 125, and validity of test result 123 creates the triplets 133 from the data set recorded 126 and the patient, time segment and location information 124.

Protected Healthcare Information and Anti Tampering with Block Chain Signature

Figure 8:
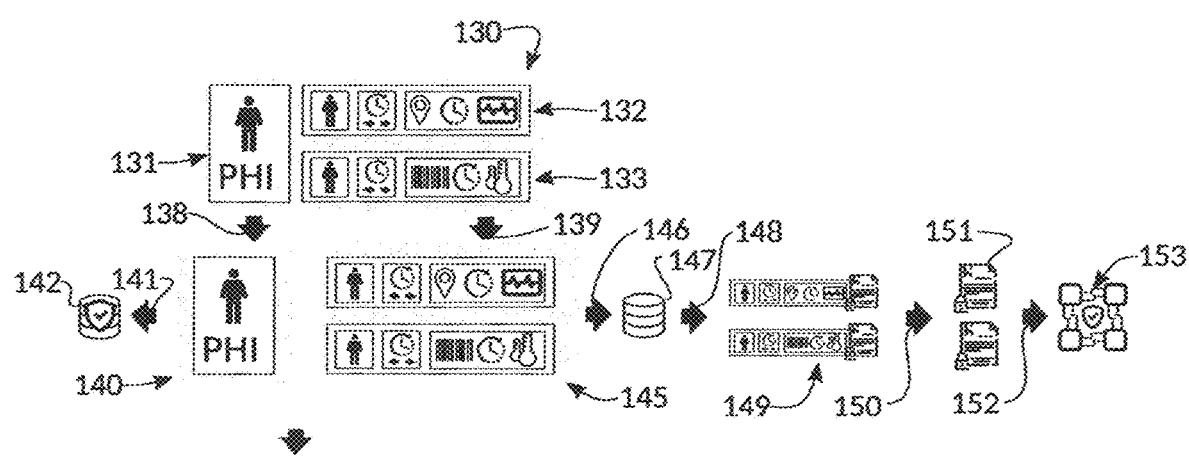
FIG. 8 is an illustration of the details of the process of storing Protected Healthcare Information (PHI) and providing a PHI data set with a block chain signature.

As depicted in FIG. 8, the process of active Positive Patient Identification and Data Validation creates multiple patient time segment data records 132, 133 associated with the patient 130 where PHI is shown, visible 131 and essential for positive patient association and the data validation process. After the modification of the previous data segments due to different information such as different times or location association, or upon creation of new triplets, they are stored 139 separately 145 from the storing 138 of the PHI 131. PHI 131 is stored 138 on third party systems 140, 141 running on a protected database system 142.

Upon confirmation of the triplet's association 145, each triplet is recorded 146 on a database 147 that triggers an automatic digital signature of each record 149 and a signature certificate is transferred 150, 151 and delivered 152 to the third-party Block Chain system 153 for safety and anti-tamper proofing of the data.

Medical Data Outputs and Deidentified Research Data Exports

Figure 9:
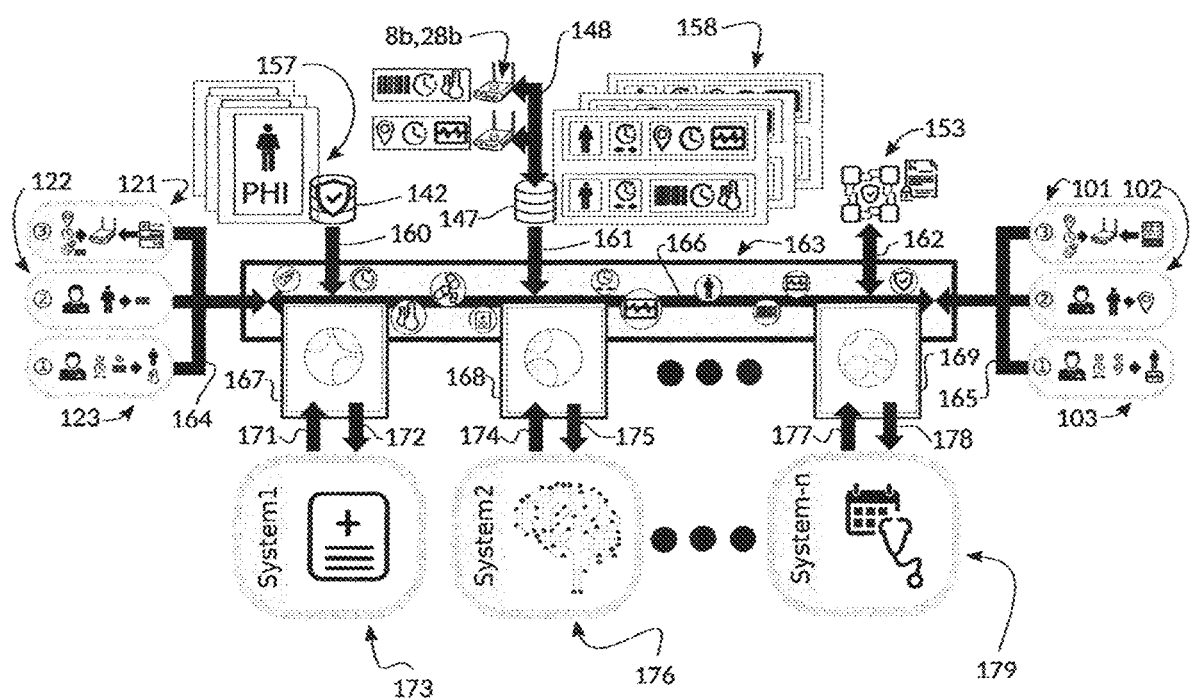
FIG. 9 is an illustration of the details of the third layer of a MDGS, data extraction and export, in an embodiment.

The third layer of the Medical Data Governance System is data extraction and single point of truth for legacy and future healthcare data systems. As depicted in FIG. 9, dependencies for adequate data outputs are defined as follows: the database 147 is populated with multiple 158 patient associated data session records 145, and the different PHI data 157 are also recorded and protected from non-authorized use 142 and interfaced to the MDGS 160. A Block Chain external service 153 is used to prevent data tampering and interfaced to the MDGS 162. Real time data is available through secure proxy tunnel 148 from bedside MDDS systems 8b, 28b. Previous location and proper time reference, metadata drivers and medical device drivers are set and ready 101. Drivers for barcode or POC inputs are properly installed to the MDDS system 8b, 28b, connected to laboratory, spot-like, multi patient medical systems 121. Patient ID is coded to barcode or POC patient code from third party systems and is available for research 122. Patient locations are available from third party systems or documented 102. Active healthcare professional(s) or an adequate automated system is assigned to verify and confirm patient id, location or barcode ID, time span, and to validate the collected data 123, 103.

True Source of Data and Data Export

As depicted in FIG. 9, by concentrating all available medical relevant data into a single source designed to handle very large, different data formats (data, metadata, values, trending, waveforms, video etc.) and providing a subset of data to each receiving subsystem 173, 176, 179 with the correct source and time reference, the Medical Data Governance System becomes the True Source of Data and guarantees the data consistency through the use of block chain signatures.

Due to the exponential data availability from growing health related devices, the risk of data not being collected, or worst being wrongly associated grows exponentially. The Medical Data Governance System opposes this trend by using the same data to augment the data affinity and isolate and indicate a possible association or data integrity errors.

An MDGS 163 data export subsystem with specific, recorded, and real time data in relation to location or to patient source can be configured 167, 168, 169 for an output system 173, 176, 179. Internal to a MDGS export data sub-item, a backbone of all data is available 166 for export drivers 167, 168, 169 access. For example, a minute-based representative value subset for a patient can be configured (exported to EMR, along with the triplets Unique Identifiers (IUD) for later more in-depth review 173, 176, 179 through a different export driver. Selected high frequency, high accuracy data can be exported, after a prolonged period like 30 or 60 days, to AI systems for machine learning processes 173, 176, 179.

In essence, data export of the same complete data acquired from medical devices, including tethered wearables via their Bluetooth descriptor, 167, 168, 169 can be different depending on the different requirements of exporting systems, and the export drivers and protocols 171, 172, 174, 175, 177, 178 can be created on demand from original, complete, high frequency, high fidelity, rich data sets originated from Digital Black Box and stored in MDGS records, time synchronized and with positive patient identification and data validation.

As mentioned above, data from patient wearables can be transmitted directly to a specific local MDDS 8a for further processing in accordance with the various methods of the invention. However, a patient roaming within or about a facility with a wearable will not have their data captured when they are out of range of any MDDS 8a receiver. Accordingly, any data generated by a roaming patient will be lost, as the wearables have only a limited storage capacity. Furthermore, there are no other commercially available Bluetooth bridges to connect Bluetooth wearables to the hospital EMR.

Figure 10:
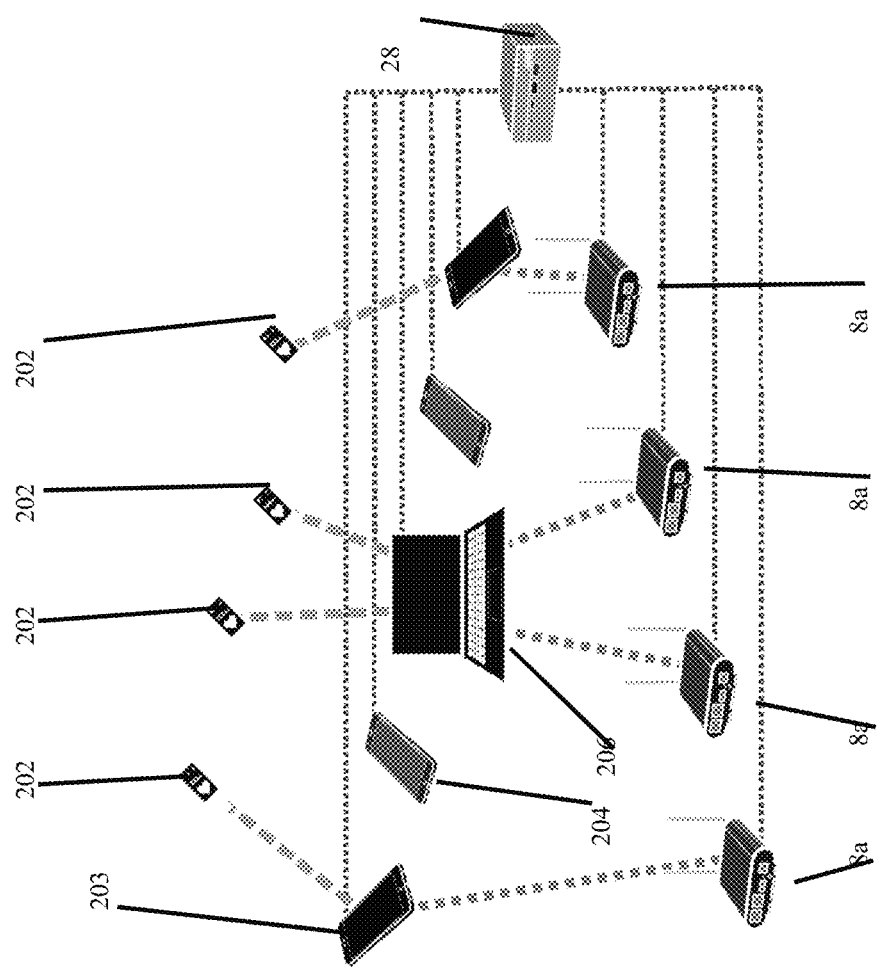
FIG. 10 is an overview of an embodiment of the invention illustrating data flow from wearables to the EMR.
Figure 11:
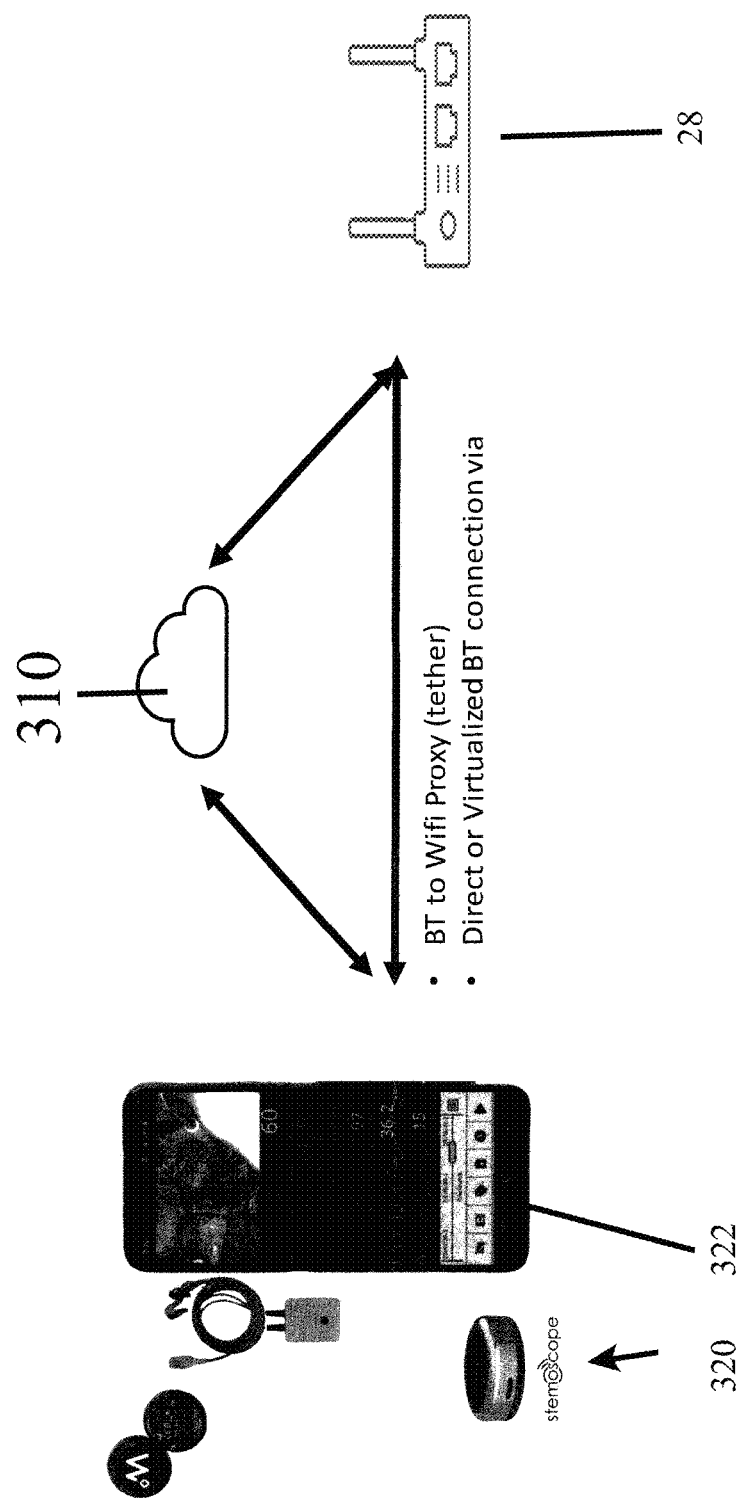
FIG. 11 is an overview of the embodiment of obtaining data from patient wearables within a facility.

Referring now to FIGS. 10 and 11, diagrammatic illustrations of an embodiment of the invention is shown. The illustration shows a mesh network using various smart devices (204, 206, etc.) to function as virtual nodes to transfer data from wearables 202 to the EMR using the methodology of MDG as described above. In accordance with the inventive concept, a novel Bluetooth proxy network is provided. The network is a virtual and distributed proxy network. This network uses the closest Bluetooth host (receiver) and tethers the connection between the wearable 202 to a central MDDS unit 28 device via Positive Patient Identification methodologies as discussed above and explained in further detail below. The central MDDS unit 28 sends the data to the EMR. Across the entire proxy network MDDS unit 28 constantly searches for better connections for each wearable 202 on the proxy network, based on signal strength as determined by the various nodes in the system, and then disconnects the old connection and establishes the new connection. A key part of the invention is that any computing device (e.g., any smartphone, tablet, computer, smartwatch, and IoT device) in the facility with Bluetooth capability can have a proxy application actively installed that makes the device a node of the proxy network. The proxy application can be downloaded from, e.g., an internet accessible server in the well-known manner to any tablet, computer, smartwatch, and IoT device within or about a healthcare facility, the application enabling the tablet 203, computer 206, smartphone 204, or IoT device to become a virtual router capable of sending data from the wearables 202 to the central MDDS 28. The proxy application may also be downloaded to the smartphone 200 of the patients. Each patient with a wearable 202 can thus become part of this virtual, distributed proxy network, and have data from the wearables 202 directly or indirectly (via the smartphone) relayed to the MDDS 8a, 28, using the tablets, computers, smartwatches, and IoT devices, etc., as intelligent proximity sensing virtual routers. Thus, every computing device in the facility including smartphones 200, tablets 203, computers 206, smartwatches and IoT devices, are actively transformed into Bluetooth hotspots and are individually converted into proxy devices, collectively working to create a virtual proxy network that seamlessly connects with the central Medical Device Data System (MDDS) 28 unit that sends the collected data to the Electronic Medical Record (EMR) and MDGS. The continuous searching and switching of wearable devices 202 among these Bluetooth hotspots enhances the reliability of data transmission, forming an intelligent routing system. The intelligent routing system ensures the seamless continuity of data from the patient by continuously searching for the best Bluetooth signal strength amongst the computing devices in the facility.

A patient's smartphone 200 may optionally be paired with one or more wearables 202 so that data from the wearables may be transmitted to the smartphone 200. Pairing the patient's phone is, however, mandatory when monitoring remotely, i.e., away from the facility, as will be described in more detail below. Each MDDS device 8a shares the Bluetooth Descriptor of every Bluetooth medical device, including patient wearables 202. The list of Bluetooth Descriptors on the various nodes of the system is populated, and continually updated by the central MDDS unit 28. Participating smartphones 204 and computers 206 (i.e., smartphones 204 and computers 206 that have the proxy application downloaded and installed) which may be mobile or stationary devices, can form virtual nodes of the inventive proxy network, the nodes operating to relay data from wearables 202 to the central MDDS device 28. By way of a non-limiting example, the smartphones 204 may be those carried by healthcare professionals within the facility, and the computers 206 may be desktop or laptop computers positioned throughout the facility in individual offices. Each participating smartphone 204 or computer 206 has the proxy application installed thereon, the application also allowing communication between the patient bedside MDDS devices 8a, and the central MDDS device 28 storing and sharing the Bluetooth Descriptors of every wearable 202 in the facility. As is known in the art, the Bluetooth Descriptor is a MAC address of the Bluetooth device, or a serial number of a device, or any unique identifier of a device. Thus, when any patient wearable 202 is within Bluetooth range of either an MDDS device 8a or a participating smartphone 204 or computer 206, the data from wearables 202 may be transmitted to the central MDDS unit 28 for further processing. It should be noted that the MDDS units 8a, 28 do all of the data processing of the signals from wearables 202, with the patient phones 200, smartphones 204, and computers 206 simply serving as physically distributed (and sometime mobile) nodes to relay data from wearables 202 roaming in or near a health care facility. It should also be noted that the central MDDS (also central server) unit 28 sends the signals from wearables 202 such that some signals will be processed and transmitted to, e.g., an EMR system for storage or transmission to a health care provider. While the present invention is described in the context of the MDGS environment, it can be readily appreciated that the method, with few or no modifications, can be practiced in any scenario where multiple Bluetooth enabled devices are distributed in a given facility or local area.

As has been mentioned, the central MDDS unit 28 and all proxy computing devices store a list of Bluetooth Descriptors. The list can be generated using multiple methods as would be apparent to one of skill in the art. For example, an NFC chip or sticker can be attached to one or more wearable Bluetooth devices 202. A health care worker can associate the device 202 with a particular patient using the NFC reader in their mobile phone 204, the phone 204 positioned to scan a patient bracelet with identifying information such as the patient's name, barcode, etc. thereon. The application on the phone 204 will read the patient's medical record number from the bracelet and confirm the identity and bed location in the facility ADT (Admitting, Discharge & Transfer) database. The local MDDS 8a will then associate the patient's medical record number with the wearable 202, and pair the wearable 202 to the bed location and associated IoMT gateway at the patient's bedside. The Bluetooth Descriptor will then be added to the active list of Descriptors in the facility stored on the central MDDS unit 28, and then the updated list of Descriptors are pushed to the computing devices and MDDS devices 8a on the proxy network. As the patient roams the facility, any MDDS 8a, 28, phone 204, or computer 206 within Bluetooth range of the patient will automatically detect the patient's wearable 202, disconnect the existing connection, pair with it, and begin receiving (raw) data therefrom. Conversely, as the patient roams the facility, any MDDS unit 8a, phone 204, or computer 206 that is about to lose connectivity due to a weak signal, will preemptively disconnect, to avoid possible data loss (from the wearable 202) from loss of signal detection. It should be noted again that the smartphones 204 of hospital/healthcare facility workers (doctors, nurses, administrators) would act as roaming virtual nodes when running the downloaded proxy application, this action effectively expanding the effective range of the inventive method. Reconnection of the wearable 202 is relatively fast, milliseconds versus minutes. The central MDDS unit 28 will determine whether to process, discard, or retransmit the data to, e.g., an EMR system.

In operation, central MDDS unit 28 monitors all of the virtual nodes created by smartphones 204, computers 206, etc. to determine the signal strength of all of the wearables 202 in the facility. The central MDDS unit 28 sends control signals to the virtual nodes to effect pairing and unpairing of the virtual nodes with wearables 202 based on the signal strength and proximity of the wearables 202. The central MDDS unit 28 will send data from the wearables to an EMR for storage or further processing.

The inventive system may also be implemented using LoRa technology. This will allow long range monitoring of wearables 202. In this scenario, the proxy device, patient phone 200 with the aforementioned proxy application installed thereon, transmits wearable data through a LoRa phone accessory to a nearby LoRa gateway. The data from the wearable 202 is transmitted to the phone 200. The nearby LoRa gateway transmits data from the phone 200 using cellular or Ethernet technology. The receiving side, e.g., a hospital EMR for example, receives sent data using cellular or Ethernet technology. Using this technique, when a patient leaves the hospital with a wearable paired phone 200, the obtained biometric data may be transmitted over long distances using LoRa technology. Patient data from wearables 202 can be monitored and transmitted to MDG via the phone 200 in real time so that, e.g., any emergency can be immediately detected.

Wi-Fi HaLow can be used to extend the range of the wearables 202. Wi-Fi HaLow enables longer range than many other IoT technology options and provides a more robust connection in challenging environments where the ability to penetrate walls or other barriers is an important consideration. Thus, a patient with a wearable 202 and with a smartphone 200 with a Wi-Fi Halow capability can connect to any network and transmit data to MDG for storage and to the EMR.

As is apparent to one of skill in the art, some data may be lost from wearables 202 during the above-described switching process. In order to limit data loss from the wearables 202, the central MDDS 28 monitors data from all wearables 202 to determine if there is a data gap. Since all wearables 202 have at least a limited storage capacity, upon detection of a data gap, the wearables can be polled by the MDDS 28 via the virtual nodes 204, etc., to fill in lost data. If it is determined that a particular wearable 202 has a data gap, MDDS 28 will initiate transmission of the stored (missing) data from the wearable 202 upon reconnection with the proxy network via the nearest node as described above. The lost data retained in the wearable 202 can then be transmitted time synchronized and inserted into the data stream from the particular wearable 202 determined to have a data gap under control of the MDDS 28, which then transmits the complete and time synchronized data from the wearable 202 to the EMR, so that the data received by the EMR has essentially no gaps.

Although particular embodiments have been described in this disclosure, many other variations and modifications will be apparent to those skilled in the art. Thus, the instant invention can be defined and limited only by the claims to be associated with this application.

The invention claimed is:

1. A method for data continuity in a mesh network of Bluetooth medical devices and computing device nodes, some of said mesh network of Bluetooth medical devices and computing device nodes contained within or about a medical facility, the method comprising the steps of:
   detecting a data gap between roaming reconnection or periodic disconnections of said computing device nodes with a specific patient medical device within the mesh network, said data gap detected by a central information Medical Device Data System (MDDS);
   initiating a process to collect missing data due to the data gap from the specific patient medical device, said process initiated by said central MDDS and instructing one of said computing device nodes to retrieve and store the missing data locally; and,
   automatically time synchronizing the stored missing data using the central information MDDS upon reconnection of the medical devices with said one of said computing device nodes; and, transmitting the missing data to an electronic medical record (EMR).

2. The method of claim 1 wherein said computing device nodes include bedside monitoring MDDS units.

3. The method of claim 1 wherein said computing device nodes include any stationary or roaming computing device within or about the facility.

4. The method of claim 1 wherein computing device nodes include smartphones, smartwatches, tablets, laptops, and desktop computers located within or about said facility.

5. The method of claim 4 wherein computing device nodes are one of smartphones, smartwatches, tablets, laptops, and desktop computers located within about said facility.

6. The method of claim 5 wherein said smartphones, smartwatches, tablets, laptops, and desktop computers may be configured as computing device nodes by downloading and installing a software application, and may be stationary or roaming.

7. The method of claim 6, wherein others of said mesh network of Bluetooth medical devices and computing device nodes are outside of said medical facility, including the steps of downloading said software application to LoRa or Wi-Fi HaLow capable computing devices; pairing one of said specific patient medical devices to one of said LoRa or Wi-Fi HaLow capable computing devices;
   connecting said one of said LoRa or Wi-Fi HaLow capable computing devices to said central information Medical Device Data System (MDDS) for transmission of medical device data thereto; whereby said mesh network is extended outside of said medical facility.

8. The method of claim 6, wherein each of said medical devices is associated with a specific patient.

9. The method of claim 6, wherein said LoRa or Wi-Fi HaLow capable computing devices are smartphones or smartwatches.

10. The method of claim 6 wherein said LoRa or Wi-Fi HaLow capable computing devices are in transport.

11. The method of claim 6 wherein said LoRa or Wi-Fi HaLow capable computing devices are positioned at a location remote from said facility.

\* \* \* \* \*